(12) United States Patent
Lacey

(10) Patent No.: US 10,478,549 B2
(45) Date of Patent: Nov. 19, 2019

(54) INTRAVENOUS LINE CONNECTION SUPPORT DEVICE

(71) Applicant: Mike Lacey, Trent, SD (US)

(72) Inventor: Mike Lacey, Trent, SD (US)

( * ) Notice: Subject to any disclaimer, the term of this patent is extended or adjusted under 35 U.S.C. 154(b) by 69 days.

(21) Appl. No.: 15/687,091

(22) Filed: Aug. 25, 2017

(65) Prior Publication Data

US 2018/0055993 A1   Mar. 1, 2018

Related U.S. Application Data

(60) Provisional application No. 62/494,920, filed on Aug. 26, 2016.

(51) Int. Cl.
*A61M 5/32* (2006.01)
*A61M 5/14* (2006.01)

(52) U.S. Cl.
CPC ........ *A61M 5/1415* (2013.01); *A61M 5/1418* (2013.01); *A61M 2005/1416* (2013.01)

(58) Field of Classification Search
CPC ........ A61M 2005/1416; A61M 5/1415; A61M 5/1418; A61M 2039/087; A61M 25/02; A61M 2025/024
See application file for complete search history.

(56) References Cited

U.S. PATENT DOCUMENTS

| 4,198,989 | A | * | 4/1980 | Hawke | A61M 25/02 128/877 |
| 4,683,882 | A | * | 8/1987 | Laird | A61M 16/0488 128/207.17 |
| 2004/0049892 | A1 | * | 3/2004 | Messina | F16L 3/12 24/279 |

* cited by examiner

*Primary Examiner* — Rebecca E Eisenberg

(57) ABSTRACT

An intravenous line connection support device holds an intravenous connection port in a static position relative to a static structure or patient to facilitate connection to the port. The device includes a support flange coupled to and extending from a base. A connection post is coupled to and extends from the base. A slit extends into the connection post defining a pair of spaced arms. Opposite faces of the spaced arms include concavely arcuate portions defining a receiver within the slit configured for receiving a connection port of an intravenous line therein. A fastener has a head and a shaft. The shaft extends through the arms and across the slit. The shaft engages the arms such that movement of the shaft selectively urges the arms together and apart wherein the fastener is configured for securing the connection port within the receiver.

8 Claims, 6 Drawing Sheets

INTRAVENOUS LINE CONNECTION SUPPORT DEVICE

CROSS-REFERENCE TO RELATED APPLICATIONS

Figure 1:
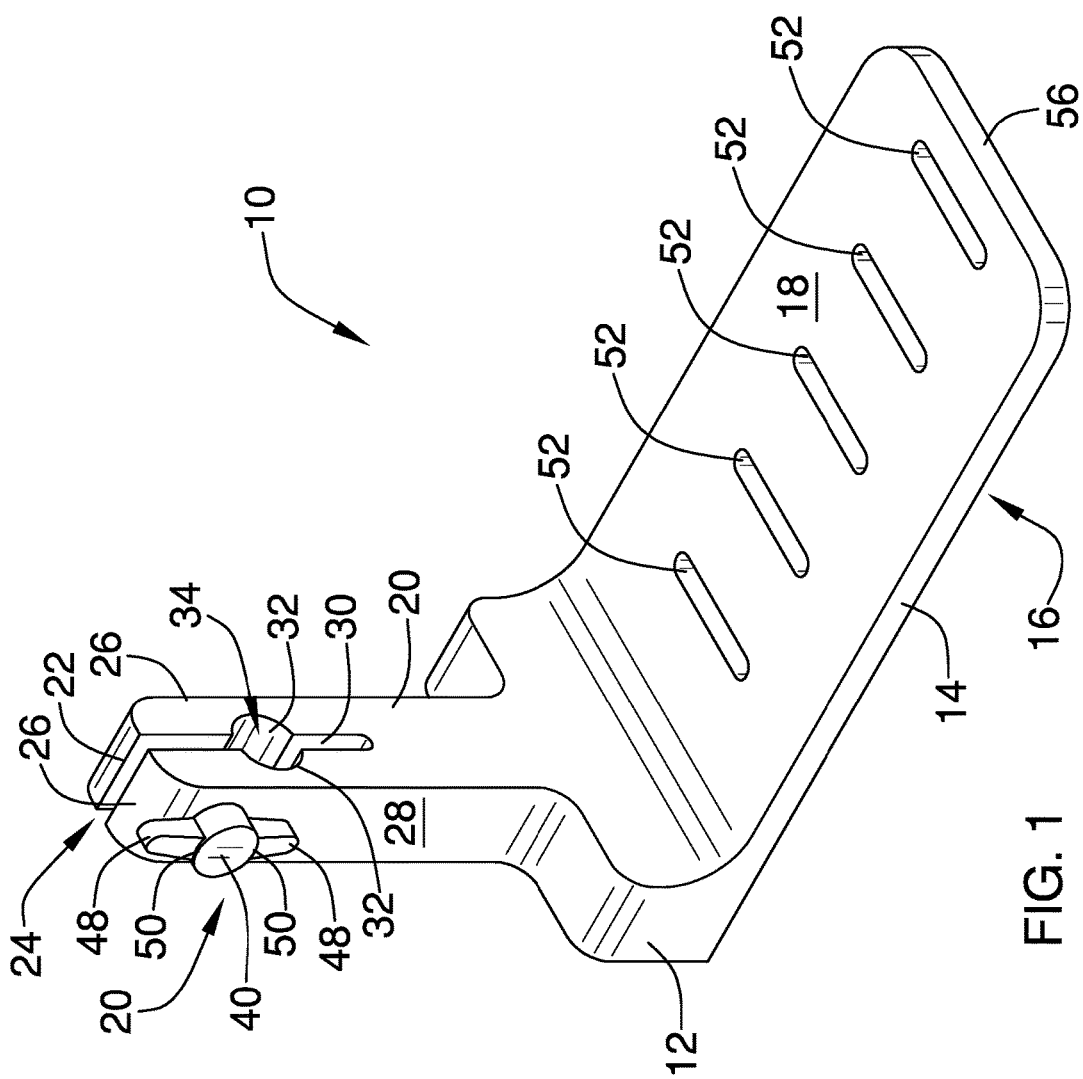

This application claims priority of the provisional application 62/494,920 filed on Aug. 26, 2016.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to support devices and more particularly pertains to a new support device for holding an intravenous connection port in a static position relative to a static structure or patient to facilitate connection to the port.

BRIEF SUMMARY OF THE INVENTION

An embodiment of the disclosure meets the needs presented above by generally comprising a support flange coupled to and extending from a base. A connection post is coupled to and extends from the base. A slit extends into the connection post defining a pair of spaced arms. Opposite faces of the spaced arms include concavely arcuate portions defining a receiver within the slit configured for receiving a connection port of an intravenous line therein. A fastener has a head and a shaft. The shaft extends through the arms and across the slit. The shaft engages the arms such that movement of the shaft selectively urges the arms together and apart wherein the fastener is configured for securing the connection port within the receiver.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 1 is a top front side perspective view of a intravenous line connection support device according to an embodiment of the disclosure.

Figure 2:
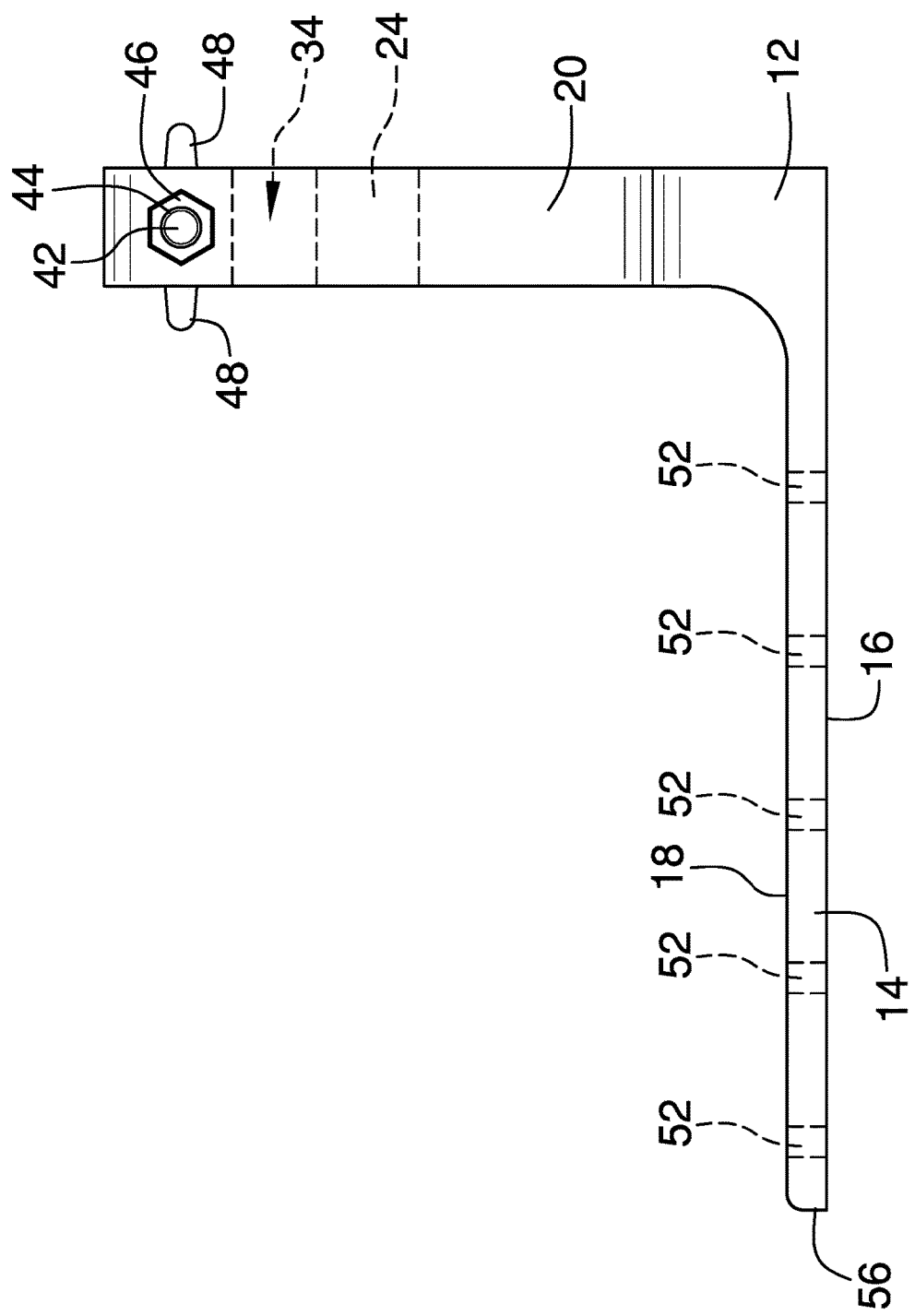
Figure 3:
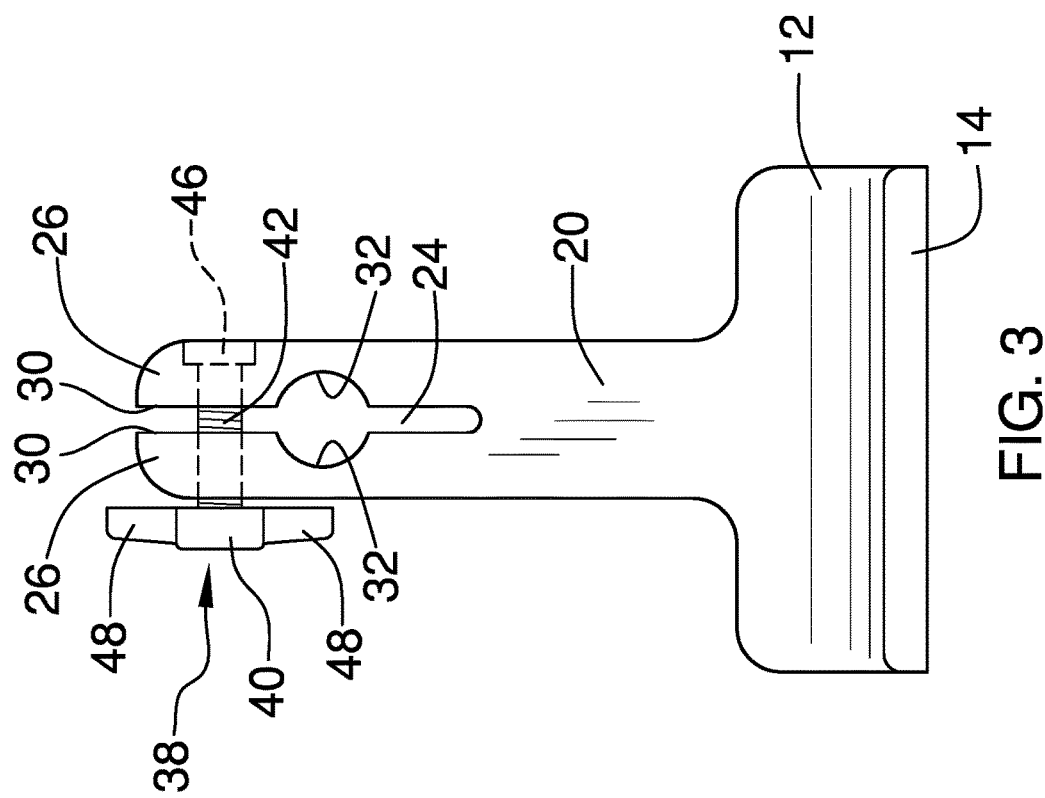
Figure 4:
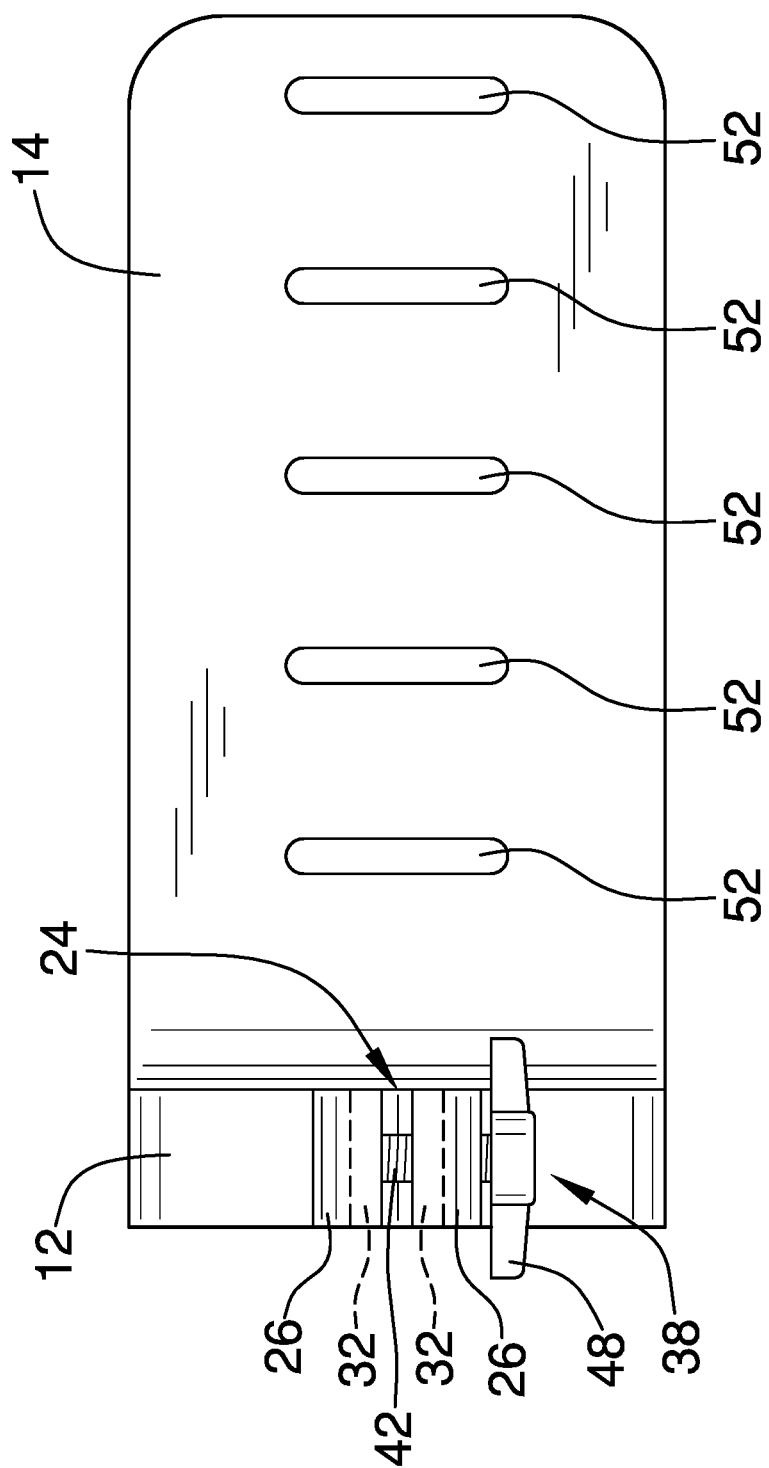
Figure 5:
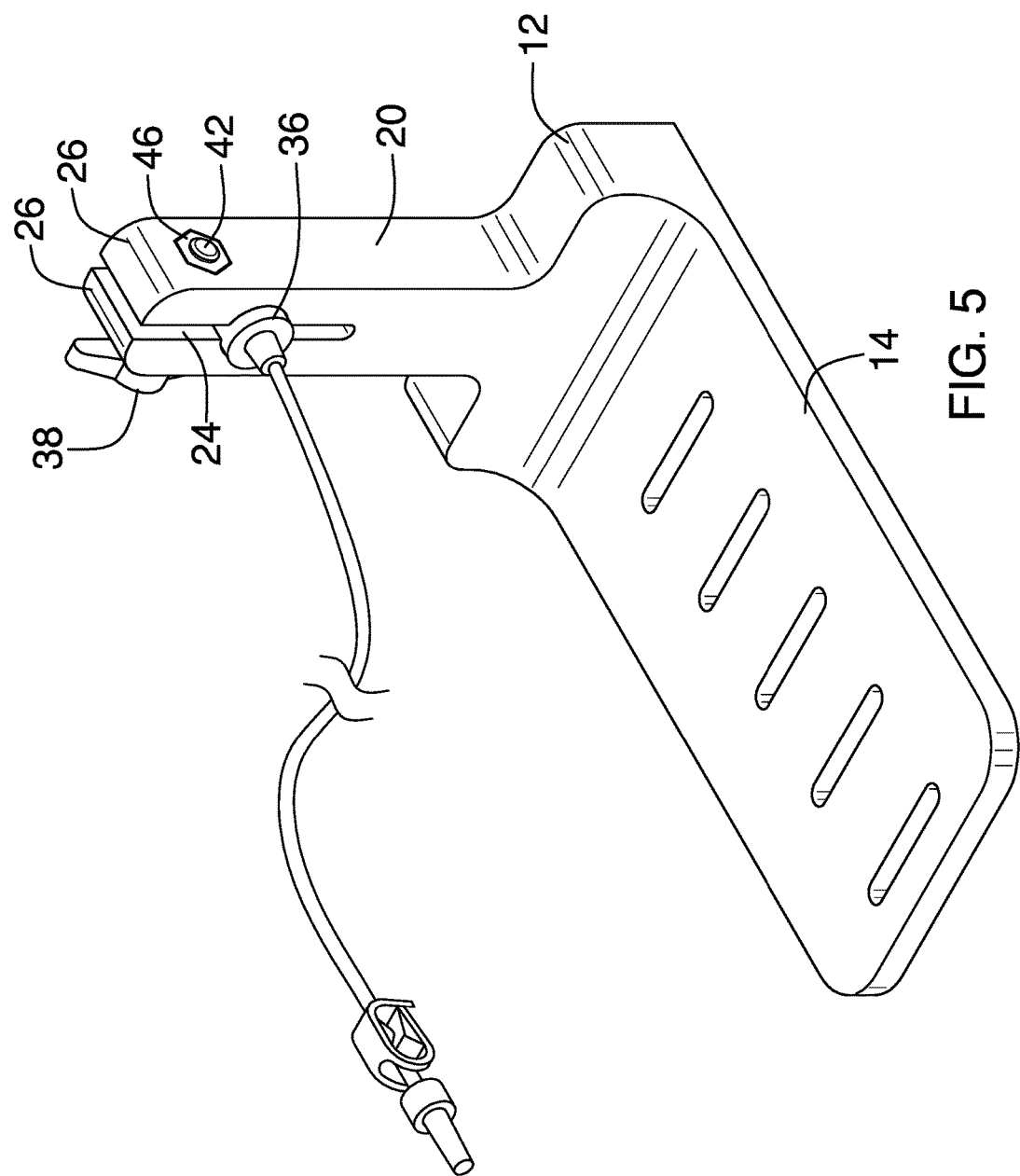
Figure 6:
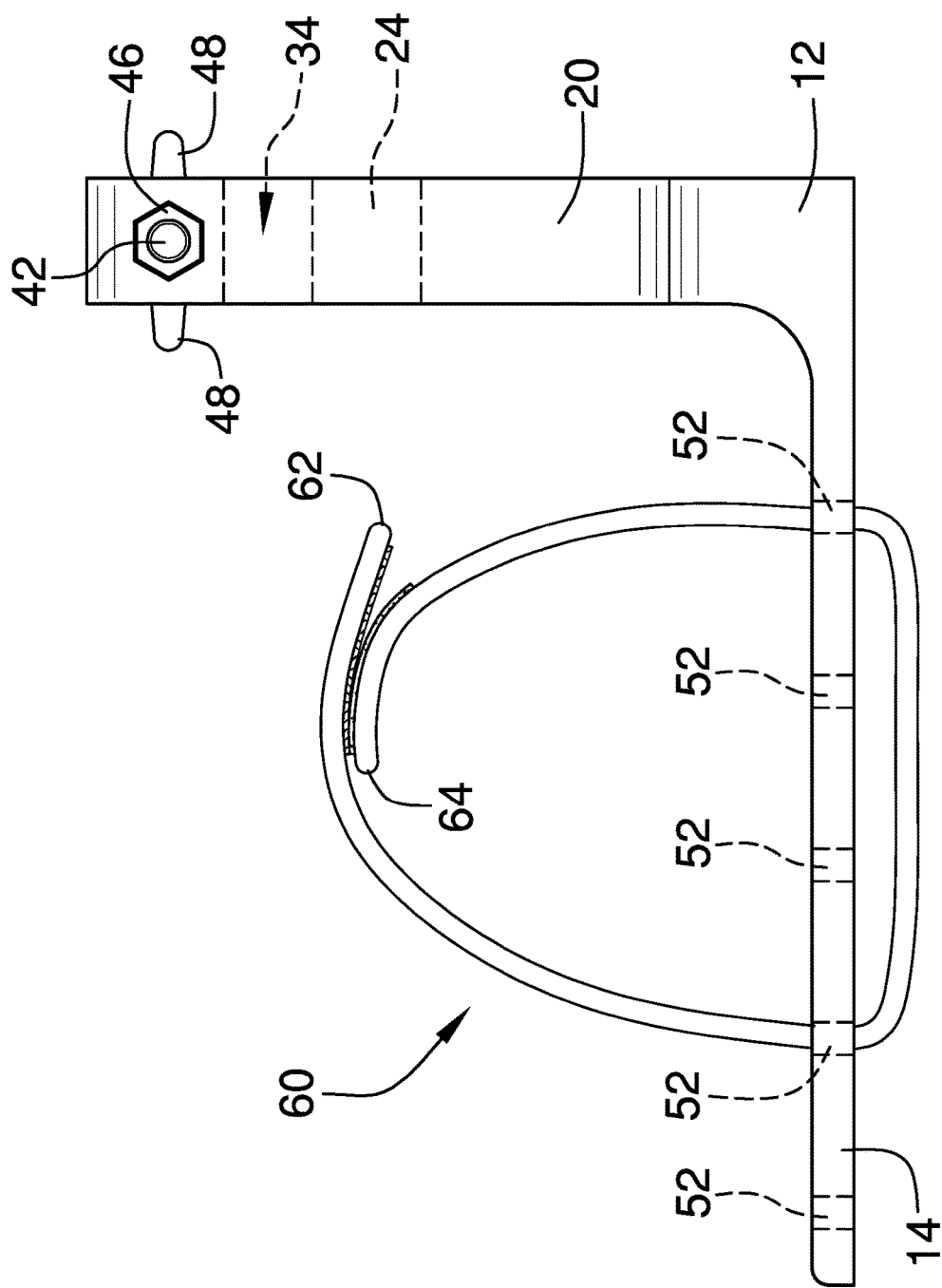

FIG. 2 is a rear view of an embodiment of the disclosure.
FIG. 3 is a side view of an embodiment of the disclosure.
FIG. 4 is a top view of an embodiment of the disclosure.
FIG. 5 is a top rear side perspective view of an embodiment of the disclosure.
FIG. 6 is a rear view of an embodiment of the disclosure.

DETAILED DESCRIPTION OF THE INVENTION

With reference now to the drawings, and in particular to FIGS. 1 through 6 thereof, a new support device embodying the principles and concepts of an embodiment of the disclosure and generally designated by the reference numeral 10 will be described.

As best illustrated in FIGS. 1 through 6, the intravenous line connection support device 10 generally comprises a base 12. A support flange 14 is coupled to and extends from the base 12. The support flange 14 may be an integral extension of the base 12 having a planar bottom surface 16 and a planar top surface 18. A connection post 20 is coupled to and extends from the base 12. The connection post 20 is perpendicular to the support flange 14 and has a distal end 22 relative to the base 12. The connection post 20 may be an integral extension of the base 12 and rigidly positioned relative to the base 12 and the support flange 14. The base 12, support flange 14 and connection post 20 may be constructed of metal, plastic, alloy, or other conventional material.

A slit 24 extends into the connection post 20 defining a pair of spaced arms 26. The slit 24 extends into the distal end 22 of the connection post 20 and is parallel to lateral outer surfaces 28 of the connection post 20. Opposite faces 30 of the spaced arms 26 include concavely arcuate portions 32 defining a receiver 34 within the slit 24 configured for receiving a connection port 36 of an intravenous line therein. The receiver may be centrally positioned along a length of the slit 24. A fastener 38 has a head 40 and a shaft 42. The shaft 42 extends through the arms 26 and across the slit 24. The shaft 42 engages the arms 26 such that movement of the shaft 42 selectively urges the arms 26 together and apart wherein the fastener 38 is configured for securing the connection port 36 within the receiver 34. The shaft 42 may be threaded and engaging threading 44 in one of the arms 26. The threading 44 may be from an inset nut 46 as shown in the drawing figures or the threading 44 may be an integral extension of the one of the arms 26 formed by boring, molding, or the like. A pair of projections 48 extends from opposite sides 50 of the head 40 wherein the projections 48 facilitate rotating the fastener 38.

Each of a plurality of slots 52 extends through the support flange 14 wherein the support flange 14 is configured for being secured to a stabilizing member such as a bed frame, arm rest, table top, or the like. Thus, the connection post 20 is configured for holding the connection port 36 in a static position relative to the stabilizing member. The slots 52 are parallel to each other, extend perpendicular to a longitudinal axis of the support flange 14, and are spaced apart along the support flange 14. The slots 52 may have outermost slots positioned adjacent to the base 12 and a distal end 56 of the support flange 14 relative to the base 12, respectively. A band 60 has a first end 62 and a second end 64. The band 60 is insertable through a selectable pair of the slots 52 and is formable into a loop 66 wherein the loop 66 is configured for securing the support flange 14 to either the support member or directly to an extremity of the person to whom the connection port 36 is attached. The device 10 may be sized to allow for the device 10 to be worn by the person for a period of time if desired. The first end 62 may be coupled to the second end 64 using hook and loop fastener or the like.

In use, the device 10 secures and holds the connection port 36 in a static position to facilitate insertion of a needle into the connection port 36. The device 10 may be used in a hospital, clinic, or at home and allows for connections to be made safely by a medical professional or even by the patient using a single hand. The device 10 obviates holding the connection port 36 to reduce the possibility of inadvertent pricking by a needle. The device 10 may be steadied or held in a static position in a variety of ways including simply by a body part being positioned on the support flange 14, connection to the support member, or a body part being coupled to the support flange 14 using the band 60. The device 10 further provides for securing the connection port 36 to the connection post 20 using only the fastener 38 which allows for very secure connection with minimal strength or grip being required.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

The invention claimed is:

1. An intravenous line connection support device comprising:
a base;
a support flange coupled to and extending perpendicularly from said base, said support flange being rigid;
a connection post coupled to and extending from said base away from said support flange, said connection post being perpendicular to said support flange;
a slit extending into said connection post defining a pair of spaced arms, opposite faces of said spaced arms include concavely arcuate portions defining a receiver within said slit configured for receiving a connection port of an intravenous line therein whereby the connection port of the intravenous line is oriented parallel to and spaced from the support flange; and
a fastener having a head and a shaft, said shaft extending through said arms and across said slit, said shaft engaging said arms such that movement of said shaft selectively urges said arms together and apart wherein said fastener is configured for securing the connection port within said receiver.

2. The device of claim 1, further comprising:
said fastener having a head, said shaft being threaded; and
a pair of projections extending from opposite sides of said head wherein said projections facilitate rotating said fastener.

3. The device of claim 1, further comprising:
said connection post having a distal end relative to said base; and
said slit extending into said distal end of said connection post.

4. The device of claim 1, further comprising said support flange having a planar bottom surface.

5. The device of claim 1, further comprising said support flange having a planar top surface.

6. The device of claim 1, further comprising a slot extending through said support flange wherein said support flange is configured for being secured to a stabilizing member such that said connection post is configured for holding the connection port in a static position relative to the stabilizing member.

7. The device of claim 6, further comprising:
said slot being one of a plurality of slots extending through said support flange, said slots being spaced apart on said support flange; and
a band, said band having a first end and a second end, said band being formable into a loop, said band being insertable through a pair of said slots wherein said loop is configured for securing said support flange to one of said support member and an extremity of the patient.

8. An intravenous line connection support device comprising:
a base;
a support flange coupled to and extending perpendicularly from said base, said support flange having a planar bottom surface, said support flange having a planar top surface, said support flange being rigid relative to said base;
a connection post coupled to and extending from said base away from said support flange, said connection post having a distal end relative to said base, said connection post being perpendicular to said support flange, said connection post being an integral extension of said base and rigidly positioned relative to said base and said support flange;
a slit extending into said connection post defining a pair of spaced arms, said slit extending into said distal end of said connection post, opposite faces of said spaced arms include concavely arcuate portions defining a receiver within said slit configured for receiving a connection port of an intravenous line therein whereby the connection port of the intravenous line is oriented parallel to and spaced from the support flange;

a fastener having a head and a shaft, said shaft extending through said arms and across said slit, said shaft engaging said arms such that movement of said shaft selectively urges said arms together and apart wherein said fastener is configured for securing the connection port within said receiver, said fastener having a head, said shaft being threaded;

a pair of projections extending from opposite sides of said head wherein said projections facilitate rotating said fastener;

a slot extending through said support flange wherein said support flange is configured for being secured to a stabilizing member such that said connection post is configured for holding the connection port in a static position relative to the stabilizing member, said slot being one of a plurality of slots extending through said support flange, said slots being spaced apart on said support flange; and a band, said band having a first end and a second end, said band being formable into a loop, said band being insertable through a pair of said slots wherein said loop is configured for securing said support flange to one of said support member and an extremity of the patient.

* * * * *